US009689793B2

(12) United States Patent
Jakli et al.

(10) Patent No.: US 9,689,793 B2
(45) Date of Patent: Jun. 27, 2017

(54) SYSTEM AND METHOD THEREOF FOR ACCURATE OPTICAL DETECTION OF AMPHIPHILES AT A LIQUID CRYSTAL INTERFACE

(71) Applicants: Antal Jakli, Kent, OH (US); Elizabeth Mann, Kent, OH (US); Piotr Popov, Kent, OH (US)

(72) Inventors: Antal Jakli, Kent, OH (US); Elizabeth Mann, Kent, OH (US); Piotr Popov, Kent, OH (US)

(73) Assignee: KENT STATE UNIVERSITY, Kent, OH (US)

( * ) Notice: Subject to any disclaimer, the term of this patent is extended or adjusted under 35 U.S.C. 154(b) by 20 days.

(21) Appl. No.: 14/621,837

(22) Filed: Feb. 13, 2015

(65) Prior Publication Data
US 2015/0233816 A1    Aug. 20, 2015

Related U.S. Application Data

(60) Provisional application No. 61/940,008, filed on Feb. 14, 2014.

(51) Int. Cl.
*G01N 21/23*    (2006.01)
*G01J 3/10*    (2006.01)
*G01N 21/77*    (2006.01)

(52) U.S. Cl.
CPC ............ *G01N 21/23* (2013.01); *G01N 21/77* (2013.01); *G01N 2021/7776* (2013.01)

(58) Field of Classification Search
CPC ............ G01N 21/23; G01N 2201/061; G01N 2201/0633; G01J 3/10

USPC ................. 356/364–369; 435/30, 288.7, 366
See application file for complete search history.

(56) References Cited

U.S. PATENT DOCUMENTS

| | | | | | |
|---|---|---|---|---|---|
| 4,561,726 A | * | 12/1985 | Goodby | ............. | C09K 19/2021 349/123 |
| 4,561,731 A | * | 12/1985 | Kley | .................... | G02B 21/088 349/1 |
| 5,420,717 A | * | 5/1995 | Tabata | ................. | G02B 5/3083 359/371 |
| 5,521,705 A | * | 5/1996 | Oldenbourg | ....... | G02B 21/0096 356/368 |

(Continued)

*Primary Examiner* — Sang Nguyen
(74) *Attorney, Agent, or Firm* — Fay Sharpe LLP

(57) ABSTRACT

Systems and methods for detection of an amphiphile at a liquid crystal interface include the production of circular polarized light. A system 100 for detecting an amphiphile at a liquid crystal interface comprises a source of white collimated light. A circular polarizer is included for circularly polarizing incoming white light. Polarized white light passes through to an LC grid including a suspended LC film and a solution in contact with the LC grid at a surface. A spectrophotometer optically detects the presence of an amphiphile at the surface by determining a change in birefringence exhibited by the suspended LC film. A method for detecting amphiphiles at a liquid crystal water interface comprises shining collimated white light on an LC cell including an LC film, polarizing the white light with a circular polarizer, adding an amphiphile to a solution in contact with the LC film, and optically detecting the presence of the amphiphile by measuring a change in birefringence exhibited by the LC film.

11 Claims, 17 Drawing Sheets

(56) References Cited

U.S. PATENT DOCUMENTS

| | | | | |
|---|---|---|---|---|
| 5,595,620 A * | 1/1997 | Takei | ............... | G02F 1/1334 156/273.3 |
| 6,040,936 A * | 3/2000 | Kim | ............... | G02B 5/008 359/245 |
| 7,292,389 B2 * | 11/2007 | Kaminsky | ............... | H04N 5/2354 348/E5.038 |
| 7,385,696 B2 * | 6/2008 | Wang | ............... | G01N 21/23 356/364 |
| 2004/0125373 A1 * | 7/2004 | Oldenbourg | ............... | G02B 21/0092 356/364 |
| 2007/0269848 A1 * | 11/2007 | Abbott | ............... | C12N 5/0068 435/30 |
| 2008/0084522 A1 * | 4/2008 | Lee | ............... | G02F 1/1334 349/88 |
| 2008/0170227 A1 * | 7/2008 | Schimming | ............... | G01J 4/04 356/364 |
| 2009/0290100 A1 * | 11/2009 | Haruta | ............... | C08J 5/18 349/75 |
| 2011/0007261 A1 * | 1/2011 | Abbott | ............... | G01N 21/21 349/199 |
| 2011/0063966 A1 * | 3/2011 | Takeshita | ............... | C08F 222/1006 369/100 |
| 2011/0306142 A1 * | 12/2011 | Lynn | ............... | G01N 21/21 436/85 |

* cited by examiner

FIG. 13

SYSTEM AND METHOD THEREOF FOR ACCURATE OPTICAL DETECTION OF AMPHIPHILES AT A LIQUID CRYSTAL INTERFACE

CROSS REFERENCE TO RELATED APPLICATIONS

This application claims priority to U.S. Provisional Patent Application Ser. No. 61/940,008, filed Feb. 14, 2014, which is hereby incorporated by reference in its entirety.

BACKGROUND

The following generally relates to systems and methods for detection of aqueous analytes such as amphiphiles at a liquid crystal interface. The system generally relates to, but is not limited to, liquid crystal—based biosensors, methods of optically detecting liquid crystal birefringence, circular polarization, and the like.

Liquid crystals (LC) are among the first choice of materials for designing devices in the information display technology sector due to their long-range orientational order and fluidity. The long-range orientational order of LCs enable them to transmit ordering at a surface into the bulk of the LC. This ordering in the bulk of the LC results in changes of the LC's effective birefringence, which is an optical property defined by a refractive index that depends on the polarization and propagation of light. This change in effective birefringence is easily detected by optical methods, enabling a quick and easy way of detecting extremely small amounts of surface molecules that have an effect on liquid crystal alignment. Accordingly, LC films may effectively act as sensors that detect when chemical or biological entities are present on an LC surface.

Surfactant-decorated LC surfaces have been developed to detect many biochemical entities and/or associated reactions. This includes the competitive binding of cholic acid (S. He, W. Liang, C. Tanner, K.-L. Cheng, J. Fang, and S.-T. Wu, Anal. Methods 5, 4126 (2013), specific enzymatic reactions (D. Hartono, X. Bi, K.-L. Yang, and L.-Y. L. Yung, Adv. Funct. Mater. 18, 2938 (2008); J. M. Brake, M. K. Daschner, Y.-Y. Luk, and N. L. Abbott, Science 302, 2094 (2003); X. Bi, D. Hartono, and K.-L. Yang, Adv. Funct. Mater. 19, 3760 (2009), bacterial catalase interactions (Q.-Z. Hu and C.-H. Jang, J. Biotechnol. 157, 223 (2012)), heavy metals (Q.-Z. Hu and C.-H. Jang, Colloids Surf. B. Biointerfaces 88, 622 (2011); (S. Yang, C. Wu, H. Tan, Y. Wu, S. Liao, Z. Wu, G. Shen, and R. Yu, Anal. Chem. 85, 14 (2013)), DNA hybridization (A. D. Price and D. K. Schwartz, J. Am. Chem. Soc. 130, 8188 (2008)), and DNA interaction with immobilized oligonucleotides (S. L. Lai, S. Huang, X. Bi, and K.-L. Yang, Langmuir 25, 311 (2009)). 5CB laden with polyacrilic acid block liquid crystalline polymers were used to detect proteins (J.-M. Seo, W. Khan, and S.-Y. Park, Soft Matter 8, 198 (2012)). Specific binding of vesicles was studied at liquid crystal interfaces laden with proteins (L. N. Tan, V. J. Orler, and N. L. Abbott, Langmuir 28, 6364 (2012)). Specific antibody interaction with surface antigen immobilized at LC interface was used for detection of hepatitis B immunocomplex (C.-H. Chen and K.-L. Yang, Anal. Biochem. 421, 321 (2012)).

Surfactants usually promote the alignment of the LC director parallel to the surfactant chains, or homeotropic, and thus on average normal to the substrate. By contrast, water promotes tangential or planar type alignment. The water—LC interface therefore is very sensitive to the presence of surfactants, such as the phospholipids that are found in biological membranes. This is the principle of the LC-based chemical and biological sensing technique introduced by Abbott et al. See R. J. Carlton, J. T. Hunter, D. S. Miller, R. Abbasi, P. C. Mushenheim, L. N. Tan, and N. L. Abbott, Liq. Cryst. Rev. 1, 29 (2013); J. M. Brake, M. K. Daschner, Y.-Y. Luk, and N. L. Abbott, Science 302, 2094 (2003), S. J. Woltman, G. D. Jay, G. P. Crawford, and G. D. J. & G. P. C. Scott J. Woltman, Nat. Mater. 6, 929 (2007).

Previous studies have employed a well-known liquid crystal, 4'-pentyl-4-cyanobiphenyl (5CB) and the homeotropic alignment coating octadecyltrichlorosilane (OTS), although recently a wider range of liquid crystals and alignment coatings have been also tested. See W. Iglesias, N. L. Abbott, E. K. Mann, and A. Jákli, ACS Appl. Mater. Interfaces 4, 6884 (2012). An LC interface with air as the alignment layer also promotes homeotropic anchoring. A biochemical sensor with air replacing the solid homeotropic alignment layer has been previously studied. See D. Hartono, X. Bi, K.-L. Yang, and L.-Y. L. Yung, Adv. Funct. Mater. 18, 2938 (2008). The advantage of using air as a substrate is that air very consistently reproduces homeotropic alignment at any level of humidity, while the quality of alignment at a solid substrate must be carefully controlled.

There is presently a lack of systems, methods, or devices that offer reliable and quantitative detection of amphiphiles at a liquid crystal interface. Present techniques use linear polarizers to analyze the alignment of the liquid crystal, which provides information not only about the birefringence, but also about the tangential distribution of the director. This additional information regarding the director is difficult to control and thus the detection method becomes largely qualitative. Additionally, present detection systems cannot effectively measure both LC film thickness and the effective birefringence of LC materials.

The detection systems, methods, and devices according to the present application include circular polarizers for analyzing the liquid crystal interface. Circular polarizers are sensitive only to birefringence, making the detection much more reliable and quantitative. The detection systems of the present application follow a new procedure that enables not only the concentration dependence of the optical path difference to be determined, but also the film thickness and the effective birefringence to be determined accurately.

In some illustrative aspects disclosed herein, a system for detecting an amphiphile at a liquid crystal interface according to an exemplary embodiment comprises a source of collimated white light, a circular polarizer for polarizing the collimated white light, an LC grid including one or more cells including a suspended nematic LC film, a solution in contact with the LC film at a surface, and a spectrophotometer which optically detects the presence of an amphiphile at the surface by determining a change in birefringence exhibited by the suspended LC film.

In some illustrative aspects disclosed herein, a method for detecting amphiphiles at a liquid crystal water interface comprises shining collimated white light on an LC cell including an LC film, polarizing the white light with a circular polarizer, adding an amphiphile to a solution in contact with the LC film, and optically detecting the presence of the amphiphile by measuring a change in birefringence exhibited by the LC film.

BRIEF DESCRIPTION OF THE DRAWINGS

FIG. 13 is a set of photographs demonstrating a "dynamic" mode of sensing DLPC phospholipid. The top row shows a slow incremental of lipid concentration. The bottom row shows where lipid concentration is initially high and held constant. The bar represents 200 μm.

DETAILED DESCRIPTION OF THE INVENTION

In various embodiments, the present application provides system, methods, and devices for detection of reliable and accurate detection of amphiphiles at a liquid crystal interface.

Figure 1:
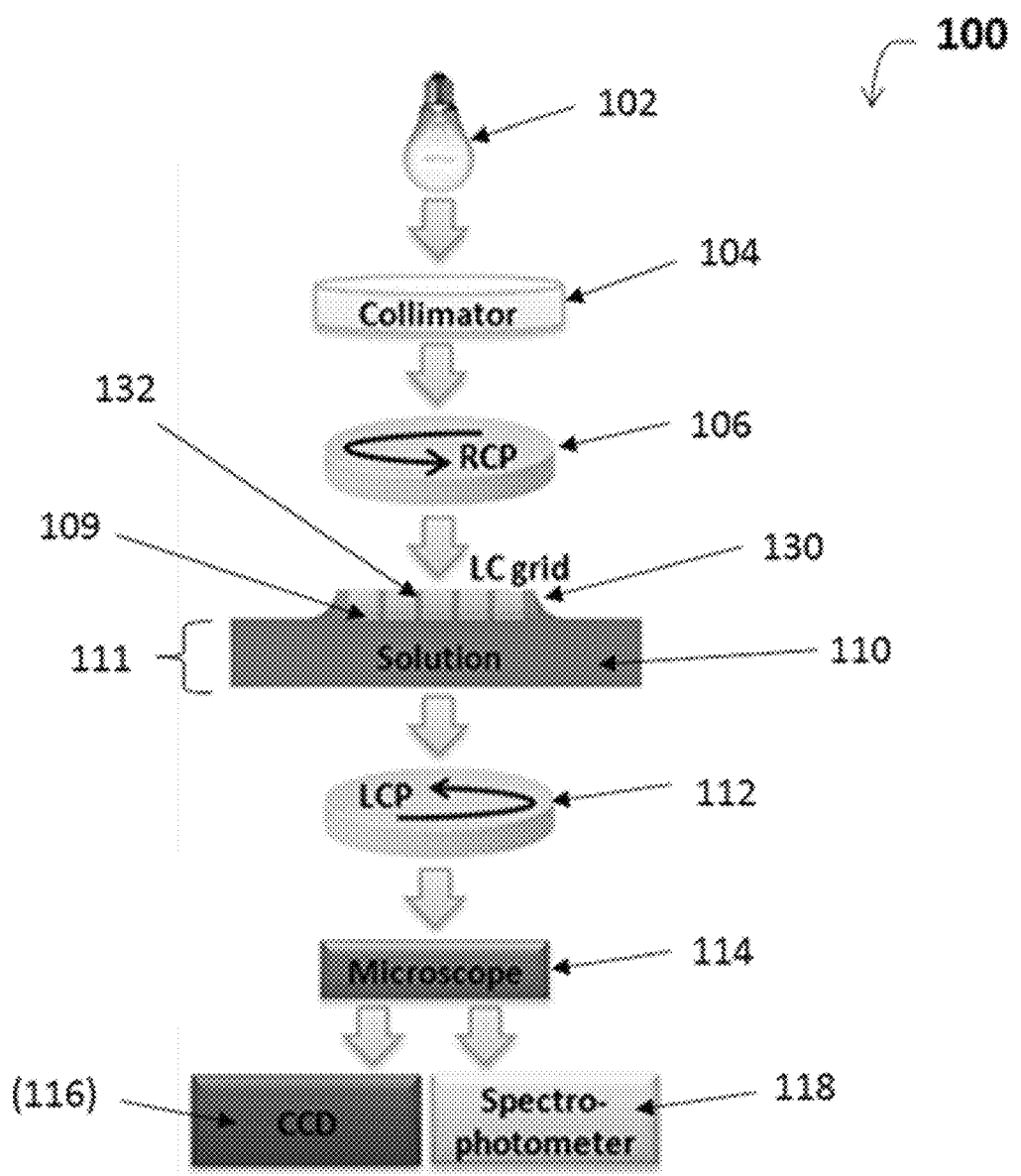
FIG. 1 is an illustration of the system for optical detection of amphiphiles at a liquid crystal water interface according to a first exemplary embodiment.

With reference to FIG. 1, a system 100 for detection of amphiphiles (or, more generally, analytes in an aqueous solution) at a liquid crystal interface according to a first exemplary embodiment is illustrated. A light source 102 shines white light on a collimator 104 to produce collimated white light. The collimated white light passes through a circular polarizer 106 to produce circularly polarized light.

The clockwise circularly polarized light travels to an LC grid 130. According to one embodiment, the LC grid 130 is a transmission electron microscopy (TEM) grid. The TEM grid 130 may be chosen from a copper square 75 mesh or nickel hexagonal 50/100 mesh Veco folding TEM grids from Ted Pella, Inc. According to another embodiment, TEM grids 130 may be around 20 μm thick and have a diameter of 3.05 mm. However, TEM grids 130 may take on other sizes as recognized by one having ordinary skill in the art.

The LC grid 108 is preferably placed above a solution 110. The solution 110 may be contained within a microscope dish 111. According to one embodiment, the solution 110 is contained within a glass-bottom microscope dish 111 obtained from Azzota. According to another embodiment, the solution 110 always stays in contact with the LC at surface 109 because it is pinned onto a rim of the LC grid 130 through one or more pins 132, as illustrated in FIG. 1.

Due to this pinning, the level of the solution 110 may vary up to 5 mm without losing contact with the LC material in the LC grid 130.

The circularly polarized light passes through the LC grid 130 and solution 110 to a circular polarizer of the opposite handedness 112. Light transmitted by the liquid crystal materials in the LC grid and the second circular polarizer 112 passes through to the microscope 114. Included within or external to the microscope 114, a CCD camera 116 may be used to take a image of the light which has passed through the LC grid 130 solution 110, and final polarizer 112, yielding an image of the LC grid. Alternatively or additionally, a spectrophotometer 118 may be used to measure birefringence of liquid crystal film within the LC grid 130. Other optical sensing devices are also contemplated.

Figure 2:
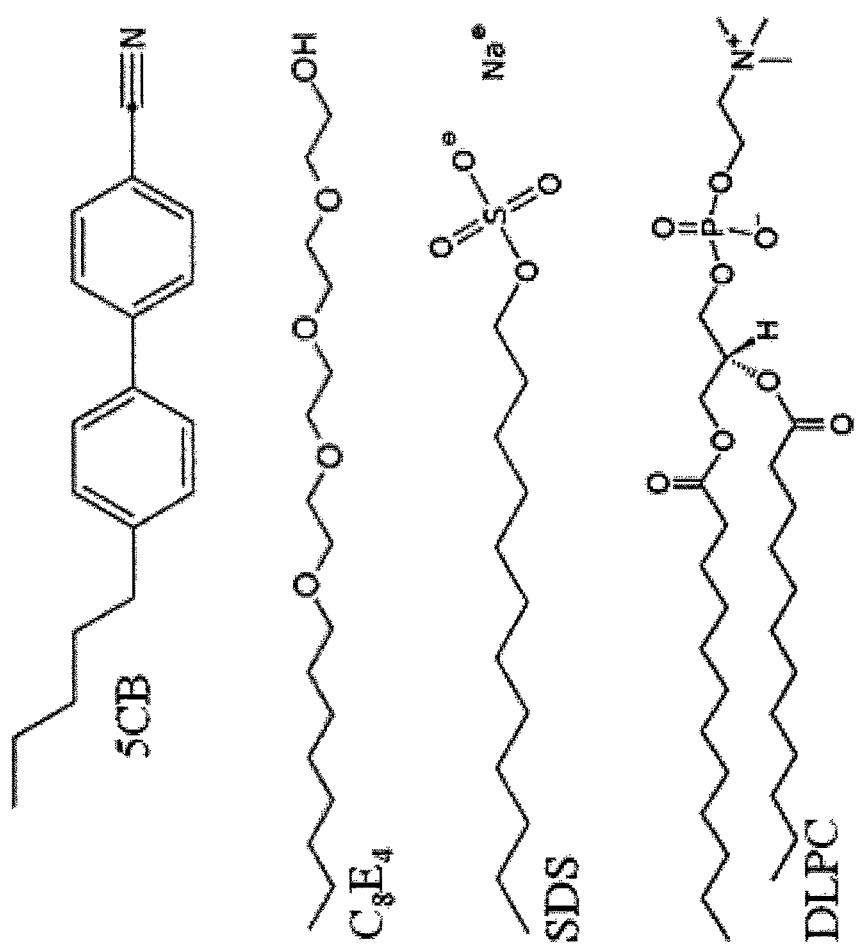
FIG. 2 is an illustration of the exemplary chemical structures of the materials which may be used in the system of FIG. 1. The (a) room temperature nematic liquid crystal 5CB, the surfactants (b) nonionic tetra(ethylene glycol) monooctyl ether ($C_8E_4$) and (c) ionic sodium dodecyl sulfate (SDS), and (4) the biologically relevant phospholipid 1,2-dilauroyl-sn-glycero-3-phosphocholine (DPLC), are illustrated.

With reference to FIG. 2, the exemplary materials, which may be used within the LC grid 130 include a nematic liquid crystal such as 4-Cyano-4'-pentylbiphenyl (5CB). Surfactants may be included such as nonionic tetra(ethylene glycol)monooctyl ether ($C_8E_4$) and ionic sodium dodecyl sulfate (SDS), both attainable from Sigma Aldritch (St Louis, Mo.). A biologically relevant phospholipid, 1,2-dilauroyl-sn-glycero-3-phosphocholine (DPLC), available from Avanti Polar Lipids, Inc., may also be used. Similar materials as known to one having ordinary skill in the art may also be used.

Figure 3:
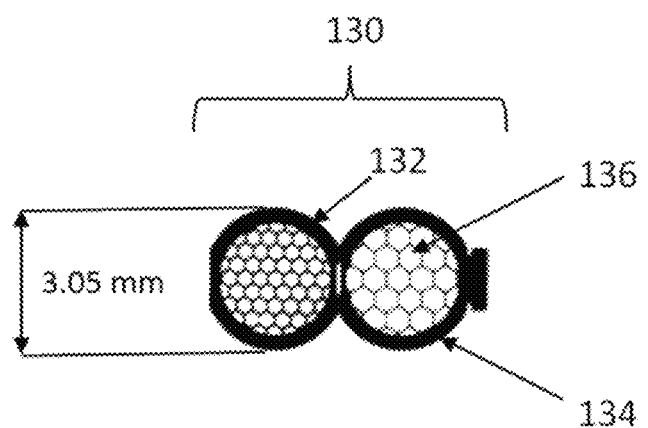
FIG. 3 is a drawings of a TEM folding grid according to one embodiment.

With reference to FIG. 3, a TEM folding grid 130 is illustrated including two twin halves 134 and 132. The TEM folding grid 130 may be held with tweezers in its empty part 132. One of the halves is a sensing part 134 which hosts the sensing LC, while the other half is the empty or holding part 132. The "sensing part" 134 may be adjusted to be parallel to the solution surface 109 by rotating the holding part 132 until the sensing part 134 is parallel to the solution surface 109, at which point the microscope can focus uniformly on it. The LC suspended in the TEM grid 130 may be stable for many weeks either in water or in air. Each part 134, 132 of the TEM grid 130 includes one or more cells 136 that can be filled with LC material.

Figure 4:
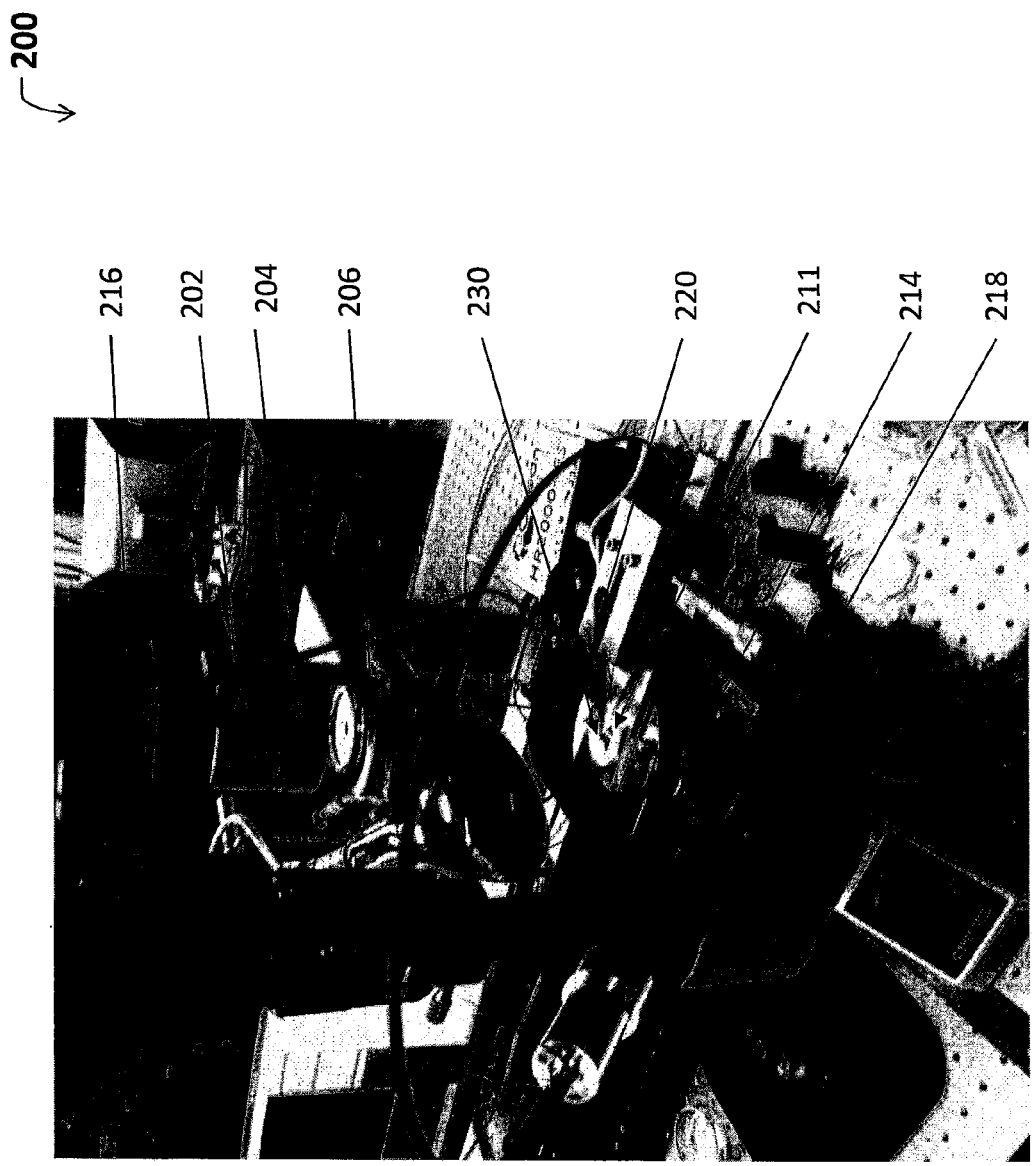
FIG. 4 is a photograph of an inverting polarizing microscope with a spectrophotometer and CCD camera. A thin LC film spanned on a TEM grid held by tweezers and immersed in aqueous solution is located on the microscope.
Figure 5:
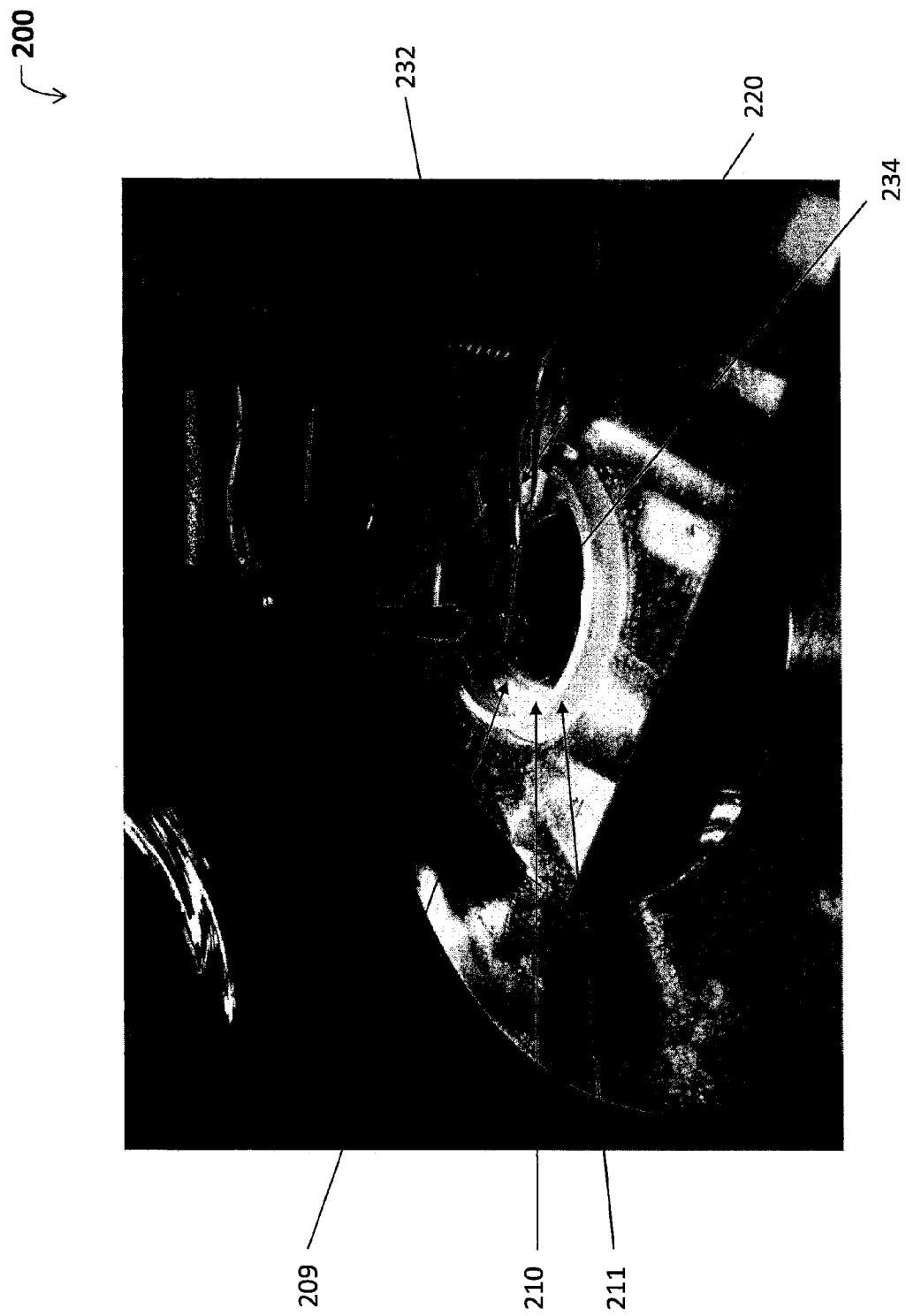
FIG. 5 is a photograph of a TEM grid held with tweezers, wherein the TEM grid is in contact with an aqueous solution from below and with air from above.

With reference to FIGS. 4 and 5, a device 200 for detecting amphiphilic molecules at a liquid crystal—water interface according to an exemplary embodiment is shown. The device 200 comprises a light source 202 which shines white light on a collimator 204 to produce collimated white light. The collimated white light passes through a right circular polarizer 206 to produce clockwise circularly polarized light. The clockwise circularly polarized light travels to an LC grid 230 filled with liquid crystal material. According to one embodiment, the LC grid 230 is a transmission electron microscopy (TEM) grid. The LC grid 230 is preferably placed above but in contact with a solution 210 contained within a microscope dish 211.

The clockwise circularly polarized light passes through the LC grid 230 and solution 210 to a left circular polarizer (not shown). Light transmitted by the liquid crystal materials in the LC grid 230 passes through to the microscope 214. Included within or external to the microscope 214, a CCD camera 216 may be used to take a photograph of the LC-filled grid 230. Alternatively or additionally, a spectrophotometer 218 may be used to measure birefringence of liquid crystal film within the LC grid 230.

With reference to FIG. 5, the device 200 of FIG. 4 is shown in a close up view. The microscope dish 211 is clearly shown, wherein the solution 210 is contained. The sensing part 234 of the TEM grid 230, which is filled with LC material, has been adjusted perpendicular to the incoming collimated light by tweezers 220 gripping the holding part 232.

Figure 6:
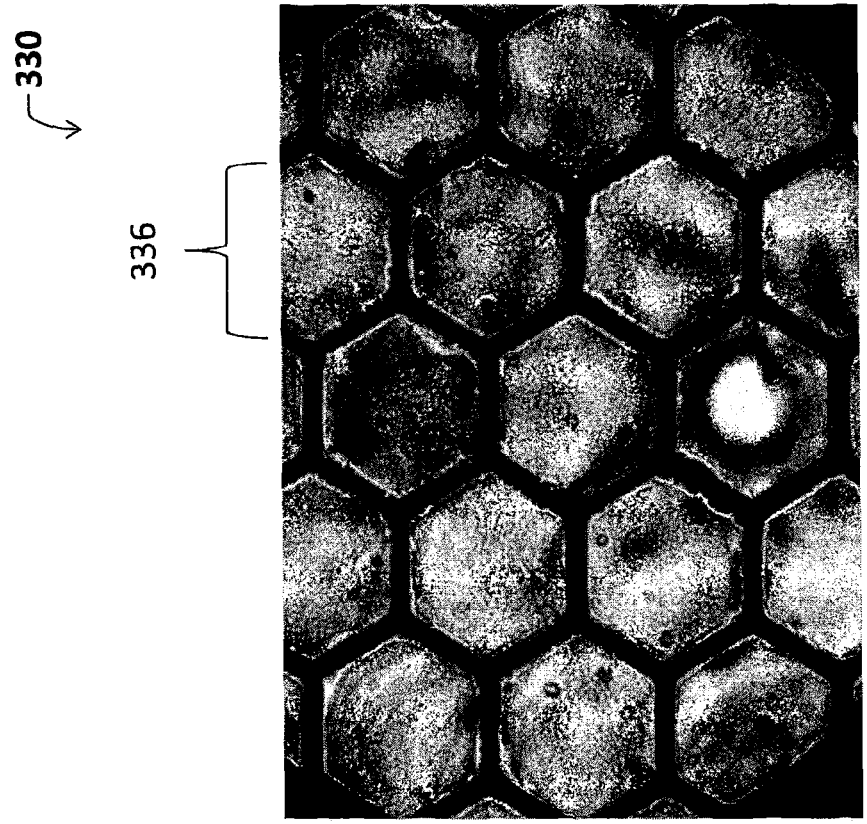
FIG. 6 is (a) a photograph of a TEM grid filled with 5CB liquid crystal. Linear polarizers have been used which produce broad dark lines; and (b), a photograph of a TEM grid filled with 5CB liquid crystal. Circular polarizers are used which remove the broad dark lines shown in FIG. 6(a).
Figure 6:

With reference to FIG. 6, a TEM grid 330 according to one embodiment is shown. A nematic LC film is suspended in one or more cells 336 the TEM grid 330. According to one embodiment, a first LC interface is locked into homeotropic alignment by a substrate or by air and second interface is exposed to the aqueous solution 310. As polarized light is transmitted through one or more cells 336, the transmission is changed due to the realignment at the aqueous interface, and the subsequent reconfiguration of the bulk LC, which provides an easily-read signal at the spectrophotometer 118 (not shown). TEM grids 330 made of gold, copper or nickel with a thickness of about 20 µm and a mesh size of a few hundred micrometers provide a convenient, readily available support.

According to one embodiment, the first interface of the grid 330 is filled with a nematic liquid crystal and is in contact with air or with a solid substrate that promotes homeotropic alignment. The second interface is in contact with water, which, in the absence of surfactants, promotes planar alignment.

The textural changes in bulk induced by the interaction of the LC at the aqueous interface can be detected optically using (by way of illustrative example) polarizing optical microscopy (POM). POM can be carried out with either linear polarizers or circular polarizers 106, 112.

Previous methods for detection of amphiphiles in liquid crystal—based biosensors employ linear polarizers. The transmitted light through a LC slab under crossed linear polarizers is described by the following formula:

$$I(\lambda) = I_0 \cdot \frac{1}{2} \cdot \sin^2(2\varphi) \cdot \sin^2\left(\frac{\pi}{\lambda} \cdot \Delta n \cdot d\right), \quad \text{(EQN. 1)}$$

where $\varphi$ is the angle between the local LC director and light polarization direction, d is the thickness of the LC slab, $\Delta n$ is the birefringence, $\lambda$ is the wavelength of the light, and $I_0$ is the intensity of the incoming unpolarized light. As water imposes random planar orientation, the tangential component of the director changes spatially through the factor $\sin^2(2\varphi)$. Therefore, the absolute value of $I(\lambda)$ is unpredictable.

Previous methods for detection with linear polarizers average $I(\lambda)$ over a large number of cells 336, assuming completely random planar orientation. However, flow and other unwanted factors impose some partial and unpredictable orientation. This unpredictability makes the observations at best semi-quantitative and requires large surface areas. Additionally, typically only an average intensity $I(\lambda)$ is measured through an average grey level in previous detection methods, which restricts the observations to the range where the effective birefringence is small, so that $\Delta n \cdot d/\lambda \ll 1$ is met.

The inventors have recognized that substituting circular polarizers 106, 112 for linear polarizers, as described herein, overcomes many of these problems associated with linear polarizers. The transmitted intensity $I(\lambda)$ between left and right circular polarizers is described by the following formula:

$$I(\lambda) = I_0 \cdot \sin^2\left(\frac{\pi}{\lambda} \cdot \Delta n \cdot d\right), \quad \text{(EQN. 2)}$$

which does not depend on φ. Accordingly, the transmitted intensity I(λ) between left and right circular polarizers does not contain information about the uncontrolled azimuthal orientation of LC director.

This lack of additional information regarding the LC director enables more reliable and quantitative detection of amphiphiles on liquid crystal interfaces. This can be seen, e.g., by comparing in FIG. 6(a) against FIG. 6(b). In FIG. 6(a), where the image was acquired using linear polarizers, dark brushes 338 appear in between crossed linear polarizers. This due to the additional information regarding azimuthal orientation of the director either parallel or perpendicular to the linear polarizers. By contrast, the LC material in FIG. 6(b), where the image was acquired using circular polarizers, exhibits uniform birefringence color seen between circular polarizers.

Additionally, averaging over large areas is no longer necessary with circular polarizers 106, 112. Rather, separate detection in each cell 336 of the TEM grid 330 becomes possible. Different materials may be placed in, and distinguished between, in each cell 336 of the TEM grid 330, thereby allowing a more quantitative detection. Each cell 336 may include different LC mixtures and/or different treatments of the surface of the liquid crystal mixtures. Measuring the spectral distribution I(λ) with a spectrophotometer 118 allows the determination of the retardation of the LC sensor. By combining measurements for three different interfacial conditions, film thickness and the effective birefringence can be determined separately.

Figure 7:
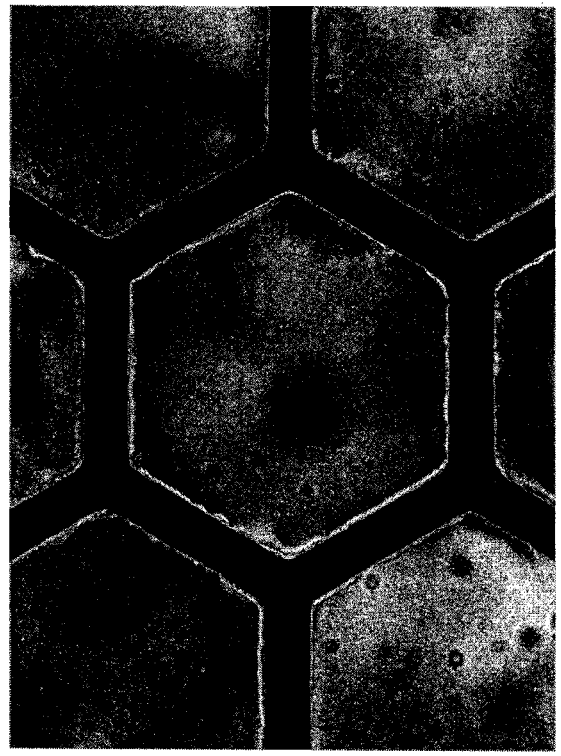
FIG. 7 is (a) a photograph of a single cell of a TEM grid filled with 5CB liquid crystal. Linear polarizers have been used which are darkening a significant area of the sensing surface; (b) a photograph of a single cell of a TEM grid filled with 5CB liquid crystal. Circular polarizers have been used which remove the dark effects seen in FIG. 7(b).
Figure 7:

With reference to FIG. 7, a single cell 336 filled with LC material is focused upon. FIG. 7(A) was imaged using crossed linear polarizers, while FIG. 7(B) was imaged using crossed (right- and left-hand) circular polarizers. Dark brushes 338 appear in between crossed linear polarizers in FIG. 7(A) due to the azimuthal orientation of the director either parallel or perpendicular to the linear polarizers. By contrast, the LC material in FIG. 7(b) exhibits uniform birefringence.

Figure 8:
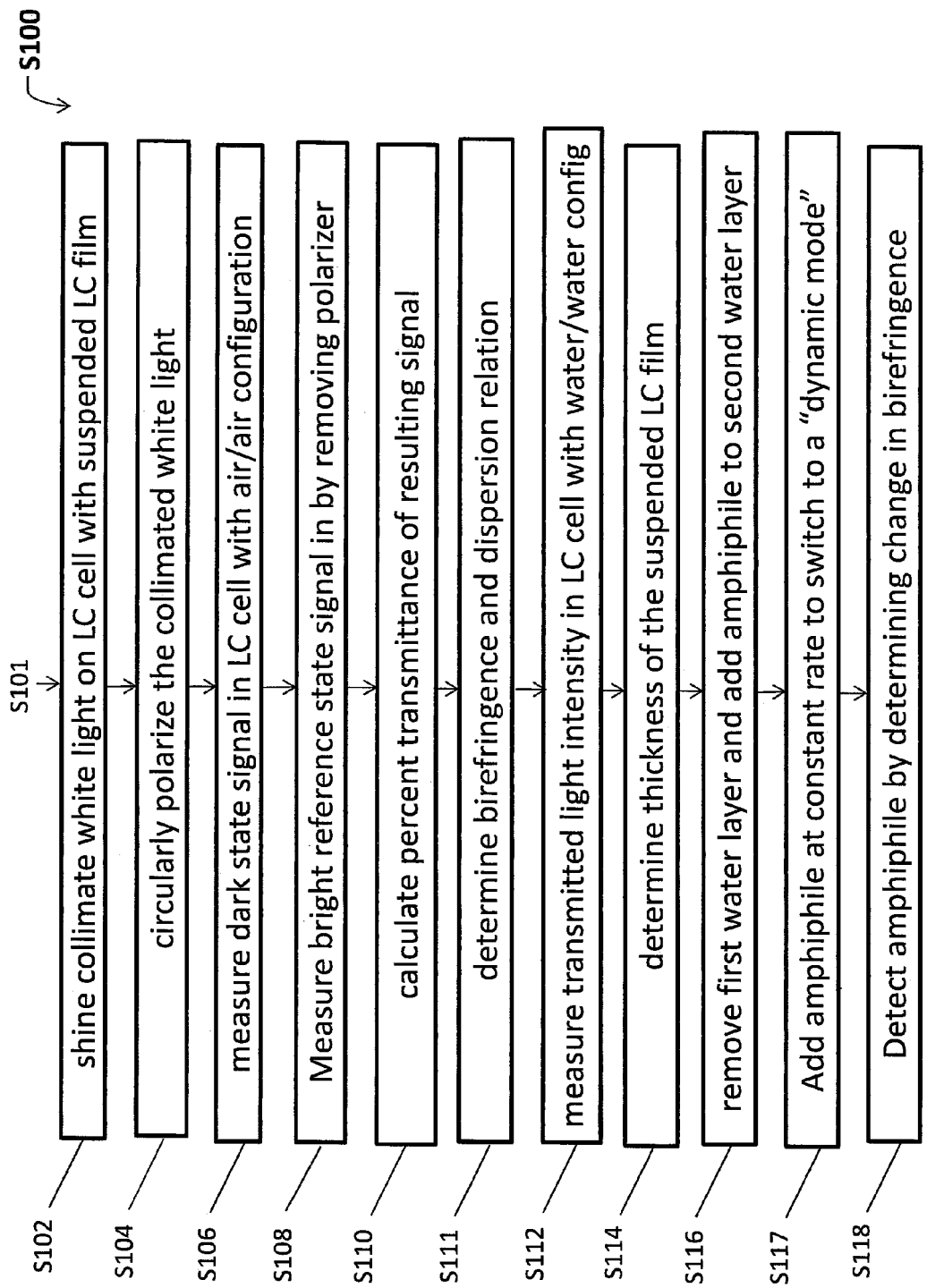
FIG. 8 is flow chart for a method for detection of amphiphiles at a liquid crystal water interface according to a first exemplary embodiment.

With reference to FIG. 8, a method S100 for detection of amphiphiles at a liquid crystal interface starts at S101.

At S102, collimated white light is shined on an LC cell including a suspended LC film.

At S104, the collimated white light is circularly polarized.

At S105, the birefringence of the suspended LC film may optionally be measured.

To measure the birefringence, the light passing through the liquid crystal film suspended in the LC cell may be measured by determining the wavelength dependence of the transmitted light intensity. Transmitted light intensity may be measured by a spectrophotomer 118, such as with an Ocean Optics HR2000+ spectrophotometer. The transmittance $\sin^2(\pi \cdot \Delta n \cdot d / \lambda)$ shows maxima and minima when $\Delta n \cdot d / \lambda = \frac{1}{2} + m$ and $\Delta n \cdot d / \lambda = m$ (where m is a positive integer), respectively. Provided that the thickness of the LC film is previously known, Δn (birefringence) may be determined by measuring the wavelengths of the maxima and minima. The larger the number of maxima and minima, the larger is the birefringence. The Δn term can be determined at all maxima and minima, which gives information about the wavelength dependence of the birefringence (dispersion) Δn(λ) of the material.

As the birefringence decreases, the number of maxima and minima decreases, too. Δn at smaller wavelengths from the position of a maximum or minimum as long as there is at least one. For the d=20 μm film, the lowest value of the birefringence that we can get from the position of the last maximum is $\Delta n_m=0.4/(2\cdot 20)=0.01$. When $\Delta n < \Delta n_m$, the transmitted light intensity is compared to that at maxima, using Equation (2) above.

For such low birefringence values it is particularly critical to know the parasitic light intensity (light leakage), which may arise from slight deviations from normal incidence, from alignment defects at the boundary of the grid and from non-perfect polarizers. The effect of parasitic light is minimized by the following procedure:

At S106, a dark state signal ($D_\lambda$) is measured wherein the LC cell is in contact with air at a first interface and second interface. This air/air interface provides homeotropic alignment, which is dark either between left and right circular polarizers or between crossed linear polarizers.

At S108, a bright reference state signal ($R_\lambda$) is measured by removing a polarizer. The top polarizer in system 100 is preferably removed so that all of the light goes through the homeotropically-aligned suspended LC film. This signal is saved as a bright reference state.

At S110, a percent transmission ($T_\lambda$) of a resulting signal ($S_\lambda$) is calculated based on the dark state signal and the bright reference state signal. The resulting signal $S_\lambda$ is then transformed to the percent transmission $T_\lambda$ by the formula:

$$T_\lambda = \frac{S_\lambda - D_\lambda}{R_\lambda - D_\lambda} \times 100\%. \qquad \text{(EQN. 3)}$$

At S111, the percent transmission ($T_\lambda$) may be used to determine birefringence and its dispersion relation.

Measured $T_\lambda$ spectra may be fitted by the formula:

$$I(\lambda) = I_0 \cdot \sin^2\left(\frac{\pi}{\lambda} \cdot \frac{\Delta n(\lambda) \cdot d}{S}\right) + I_p, \qquad \text{(EQN. 4)}$$

in which $I_0$ is the incoming light intensity, α,β,γ are the Cauchy coefficients for dispersion of the nematic LCs, $$\Delta n(\lambda) = \alpha + \frac{\beta}{\lambda^2} + \frac{\gamma}{\lambda^4}, \qquad \text{(EQN. 5)}$$

$I_p$ is the additional parasitic light intensity and S is a scaling parameter. For 5CB α=0.1569, β=0.0029 μm², and γ=0.0016 μm⁴, according to Jun Li et. al. See M. I. Kinsinger, D. M. Lynn, and N. L. Abbott, Soft Matter 6, 4095 (2010). The parameter S scales the 5CB birefringence depending on the angle between LC director and LC/water interface plane:

$$\Delta n_{\mathit{eff}}(\lambda) = \frac{\Delta n(\lambda)}{S}, \qquad \text{(EQN. 6)}$$

In Eq. (4) the variable is the wavelength λ, fitting parameters are $I_0$, $I_p$, S and α,β,γ, d are held fixed. The scaling parameter was introduced to reduce the number of fitting parameters and improve the stability of this nonlinear fit. It assumes that the dispersion does not change with variations in molecular tilt through the cell.

The measured I(λ) gives the birefringence if film thickness is known. Determining the film thickness precisely is difficult task however, because the thickness of the grid can vary, and because the grids can be underfilled, or overfilled.

The first case usually leads to a variation of the film thickness as the liquid crystal wets the grid, causing a meniscus. This could easily be identified by the spatial variation of the birefringent color. However, it is also possible that the liquid crystal can have an extra layer that spans the entire film including the grid area. This results in uniform birefringence, which cannot be identified by the varying birefringence color, and would lead to an overestimate of the birefringence.

To exclude this error, $I(\lambda)$ may be measured when the cell was completely immersed under water. At S112, transmitted light intensity is measured in the presence of the LC cell in contact with water at a first and second interface. The water/LC/water interfaces in S112 orients 5CB molecules parallel to the interface, so $\Delta n_{eff} = \Delta n$ i.e., S=1 in Eq. (6).

Therefore after S112, the fit according to Eq. (4), with S=1, may be used to accurately determine the film thickness d of the suspended LC film. This film thickness d should not change when the upper layer of water is evaporated and the surfactant is added to the lower layer of water. At S114, the thickness of the suspended LC film is determined based on the transmitted light intensity measured in S112.

By this procedure of accurately measuring film thickness in S110 and S112, $\Delta n_{eff}$ as determined in S111 or in later steps of method S100, may be measured more accurately.

At S116, water is removed to leave the first interface exposed to air and an amphiphile is added to the water in the second interface. A fixed concentration of amphiphile is added to the second interface, wherein detection occurs according to a "steady mode." With reference to FIG. 2, the amphiphile may be a non-ionic surfactant, e.g. $C_8E_4$, or an ionic surfactant, e.g. SDS. The amphiphile may also be a phospholipid, e.g. DLPC.

At S117, the amphiphile added in S116 is added to the second interface at a constant rate in order to switch detection from a "steady mode" to a "dynamic mode." Based on the dynamics and concentration range of the amphiphile, one may use the system 100 in a "steady" mode, which was studied by Kinsinger et. al. by depositing the lipid Langmuir monolayers at a fixed density (M. I. Kinsinger, D. M. Lynn, and N. L. Abbott, Soft Matter 6, 4095 (2010), or could switch to a "dynamic" mode, where the sensing range depends on the rate of the concentration change.

At S118, the presence of the amphiphile is determined by measuring a change in birefringence.

Also disclosed are LC-based biosensor devices attached to the camera of a smart phone. In order to achieve additional optical zoom, an external lens (e.g., an "Olloclip") can be attached to the phone. Conoscopic (or "fisheye" microscopy may be conducted to measure birefringence using a cell phones (e.g., an iPhone4S). To convert the compact setup into a biosensor device, a pair of polarizers can be added. The test-sample can then be introduced into a glass capillary (e.g., a small rectangular glass capillary) containing a TEM grid filled with LC material.

Further disclosure is provided in the form of the following examples. The examples provided are merely representative of the work that contributes to the teaching of the present application. The examples are merely illustrative and are not intended to limit the disclosure to the materials, conditions, or process parameters set forth therein.

Example 1: Comparison of Transmission Signals Obtained when Using Linear Crossed Polarizers and Circular Polarizers with Water/Air Configuration LC Interface As illustrated in FIG. 9, the textures and the corresponding wavelength dependence of the transmitted light intensities are seen in between linear and circular polarizers.

FIG. 9(a) compares the textures and the wavelength dependence of the transmitted light intensity for a well-filled individual cell. The texture seen between circular polarizers is fairly uniform with a green birefringence color, whereas the same area looks inhomogeneous with dark brushes when viewed between crossed linear polarizers. The corresponding spectra show maxima and minima at the same wavelengths (indicating nearly the same birefringence), but the intensity is much larger between the circular polarizers.

Figure 9:
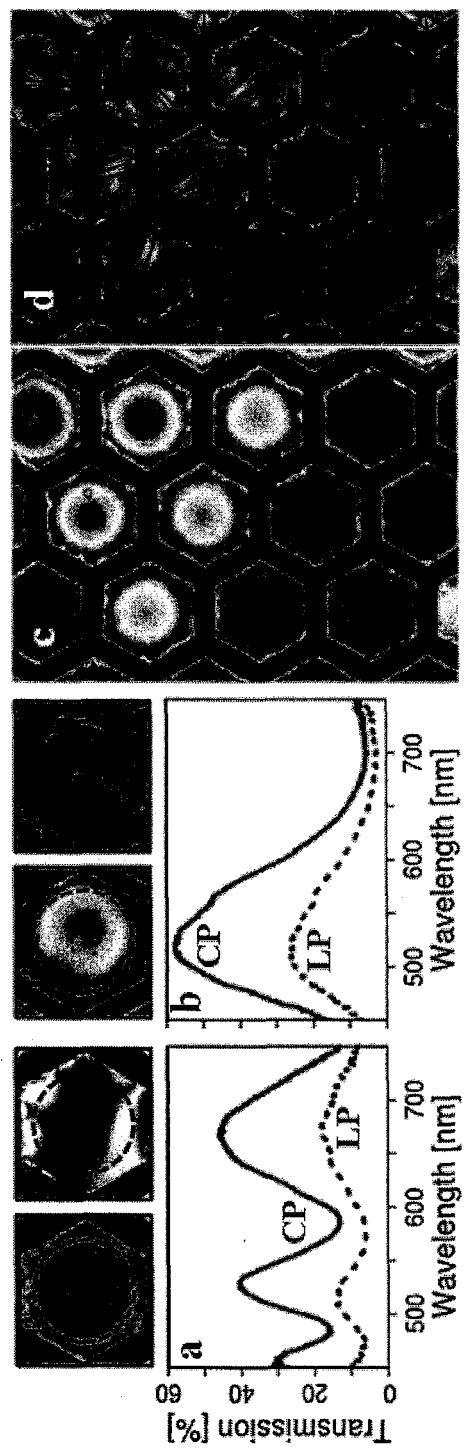
FIG. 9 shows a comparison of transmission signals obtained when using linear crossed polarizers (LP) and circular polarizers (CP) with water/air interfaces. Graphs of transmission (%) versus wavelength (nm) are illustrated for (a): an evenly filled cell; and (b): an underfilled cell exhibiting interference rings due to a meniscus. The photographs above the graphs show the texture of the single cells corresponding to situation (a) and (b). In another photograph (c), the texture of a cell array between circular polarizers is shown. In yet another photograph (d), texture of a cell array is shown between crossed linear polarizers. The diameter of the hexagonal cells is 200 μm. Spectrophotometer measurement was collected only from within the dashed blue circles and not from entire cells.

FIG. 9(b) shows the textures and the corresponding transmission spectra for one example of an underfilled grid. In this case, a centered defect line with strength +1 with four brushes is seen between linear polarizers, but appears as only a small dark dot between circular polarizers. In addition, the images with circular polarizers show circular rings with decreasing birefringence colors, revealing that the thickness of the liquid crystal decreases toward the center of the grid. The appearance of defects is uncontrolled and they do not always appear when circular meniscus rings are present, as evidenced by the top right images of FIG. 9 (c,d).

Films without a meniscus provide a determination of the cell thickness in the water/water case, following the procedures described above. A correct value of the effective birefringence can be readily determined from the data in FIG. 9(a), while the data from FIG. 9(b) would first require determining the thickness distribution. It is much less time consuming to simply choose cells without a meniscus.

In the air/air mode, the 5CB molecules are arranged perpendicular (homeotropic) with respect to the grid plane. Accordingly, the textures appear homogenously black across the entire cell, except at the boundaries of the grid. The LC molecules within several microns of the boundary are mostly aligned parallel to the grid plane.

Gold, nickel and copper grids were all found to produce this short-range homeotropic anchoring. Measured spectra are not collected from the entire cell area, but rather from an inner diameter. The inner diameter of the hexagonal cell is 200 µm, while only the area of a circle with diameter of ~170 µm was used to collect the spectra as shown in 9(a) and 9(b) by dashed blue circles. In this way, it is possible to avoid the light leakage that additionally comes from the anchoring of LC to the metal grid.

FIGS. 9(c) and (d) show a number of cells between circular and linear polarizers, respectively. The images with circular polarizers, in FIG. 9(c) show some cells (in the bottom-left of the image, about ⅓ of the whole area) that exhibit circular ring patterns, indicating they are underfilled. We observed that this large percentage of underfilled cells is quite typical even when one side of the film is in contact with air, and becomes even worse in the traditional homeotropic substrate/water configuration, because during immersion under water some of the LC tends to get washed away. This illustrates the importance of identifying and excluding underfilled cells from the birefringence measurements to achieve precise sensing.

Figure 10:
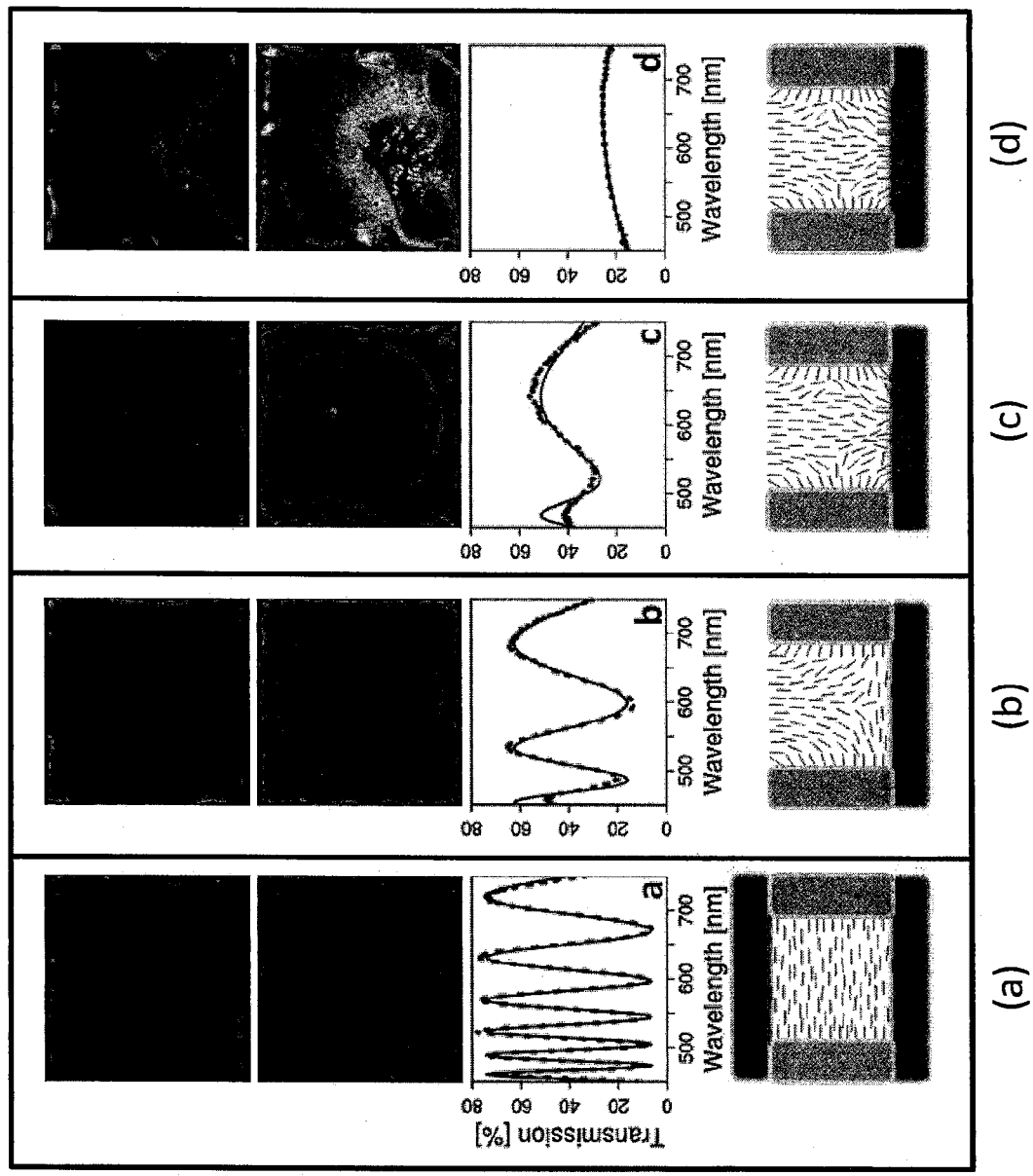
FIG. 10 is a combination of photographs, graphs, and illustrations showing optical textures and the wavelength dependence of transmitted intensities between circular polarizers in different LC/water/air/surfactant combinations. The top row photographs show the optical textures of LC materials in different situations (a-d) as viewed between crossed linear polarizers. The second row photographs show optical textures of LC materials in different situations (a-d) between circular polarizers. The third row graphs plot the transmission (%) versus wavelength (nm) to convey the wavelength dependences of transmitted intensities measured on single cells in different situations (a-d) between circular polarizers together with a nonlinear fit using equation. The bottom row illustrations show substrate-less configurations in (water/water interfaces, using S=1 and finding d=23.53±0.02 μm; (b) water/air interfaces, S=2.355±0.001; (c) Solution (C=2.5 mM $C_8E_4$)/air interfaces S=4.298±0.008; (d) solution (C=4.5 mM $C_8E_4$)/air interfaces S=12.58±0.04.

Example 2: Optical Textures, the Wavelength Dependence of Transmitted Intensities Between Circular Polarizers in Different LC/Water/Air/Surfactant Combinations As illustrated in FIG. 10, textures were compared between crossed linear polarizers (top row) and between circular polarizers (second row) to show the wavelength dependences of the transmitted intensities measured between circular polarizers. Eq. (3) was used together with the nonlinear fit using Eq. (4) to produce the graphs in the third row. The graphs correspond to four different combinations of LC/water/air/surfactant as demonstrated in the four different configurations illustrated in the bottom row.

FIG. 10(a) represents a cell that is completely immersed under water. As explained above, here we set S=1 in Eq. (6) to obtain an accurate value of the film thickness, which presumably will not change upon the evaporation of the top water layer. Although it is rare due to the hydrophobic nature of the thermotropic LC, underfilled cells with ring pattern may appear as seen in 9(b) and in top corner of (c,d). Ring patterns never develop during the experiment, but only at the moment when the LC is filled into the grid or at the moment of complete immersion into water, suggesting that once formed, the film thickness remains constant in time.

In FIG. 10(b) the LC cell is in contact with water at the bottom (planar alignment) and with air on top (homeotropic alignment). This results in a hybrid alignment exhibiting a smaller effective birefringence, which is evidenced by the reduced number of maxima (3) and minima (2). The scaling parameter for Cauchy coefficients is S=2.355±0.001. The situations when 2.5 mM and 4.5 mM surfactant $C_8E_4$ are added to the water are shown in (c) and (d), respectively. As evidenced by the decreased number of maxima (2 for (c) and 1 for (d)) and minima (1 for (c) and 0 for (d)) the birefringence further decreases upon addition of surface-active molecules to the water. In spite of the small number of extrema, the scaling parameters could be still determined from the fitting Eq. (4). The scaling parameter in (c) is S=4.298±0.008 and it is further increased in (d) to S=12.58±0.04 due to the $C_8E_4$ increased concentration.

The dark brushes that appear even at zero surfactant concentrations in between crossed linear polarizers are due to the azimuthal orientation of the director either parallel or perpendicular to the linear polarizers, as evidenced by the uniform birefringence color seen between circular polarizers. This demonstrates the advantage of the circular polarizers. Additionally, they are easier to use, since they do not need to be precisely oriented with respect to each other, in contrast to linear polarizers that need to be set perpendicular to each other. The inhomogeneous areas seen in between circular polarizers in the second row of FIG. 10 are steady at a given concentration, thus indicating inhomogeneous surfactant distribution. The reasons for this inhomogeneous distribution are unclear, but their nature depends strongly on the surfactant, its concentration, and addition history; these would be interesting to study further.

Figure 11:
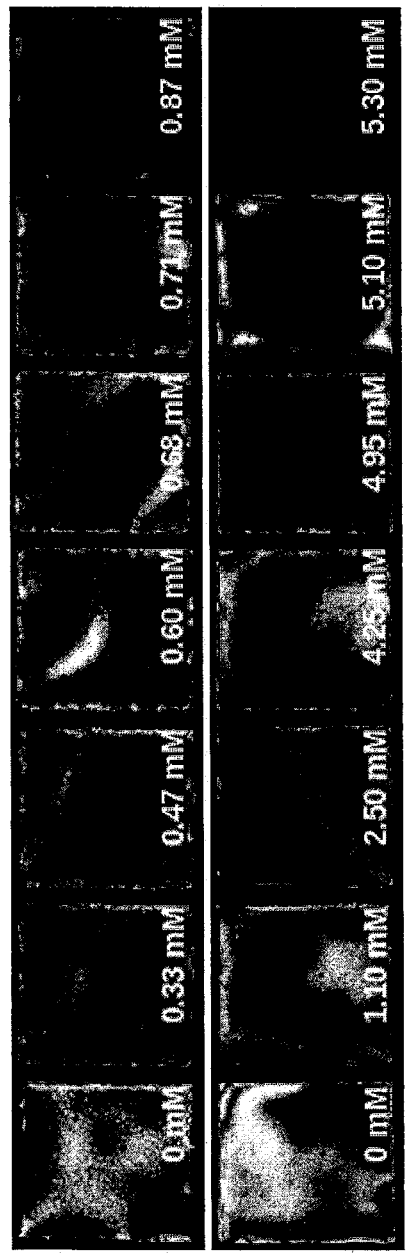
FIG. 11 is a set of photographs of LC texture comparing the effect of SDS and $C_8E_4$ on the alignment of the liquid crystal 5CB. The top row shows LC 5CB, ionic surfactant, and SDS. The bottom row shows LC 5CB and non-ionic surfactant, $C_8E_4$. Textures are obtained using linear crossed polarizers.

Example 3: Comparison of the Effect of SDS and $C_8E_4$ on the Alignment of the Liquid Crystal 5CB As illustrated in FIG. 11, qualitatively compares the effect of $C_8E_4$ (CMC=8.5 mM) non-ionic surfactant with the ionic SDS (CMC=8.2 mM). Although the induced textures seen by polarizing optical microscopy (POM) are very similar, the concentration ranges are very different; about 6 times more $C_8E_4$ is needed to drive the hybrid geometry completely into homeotropic state. Since the CMC values for both surfactants are almost the same, we attribute this difference to a better affinity to 5CB of SDS compared to $C_8E_4$.

Figure 12:
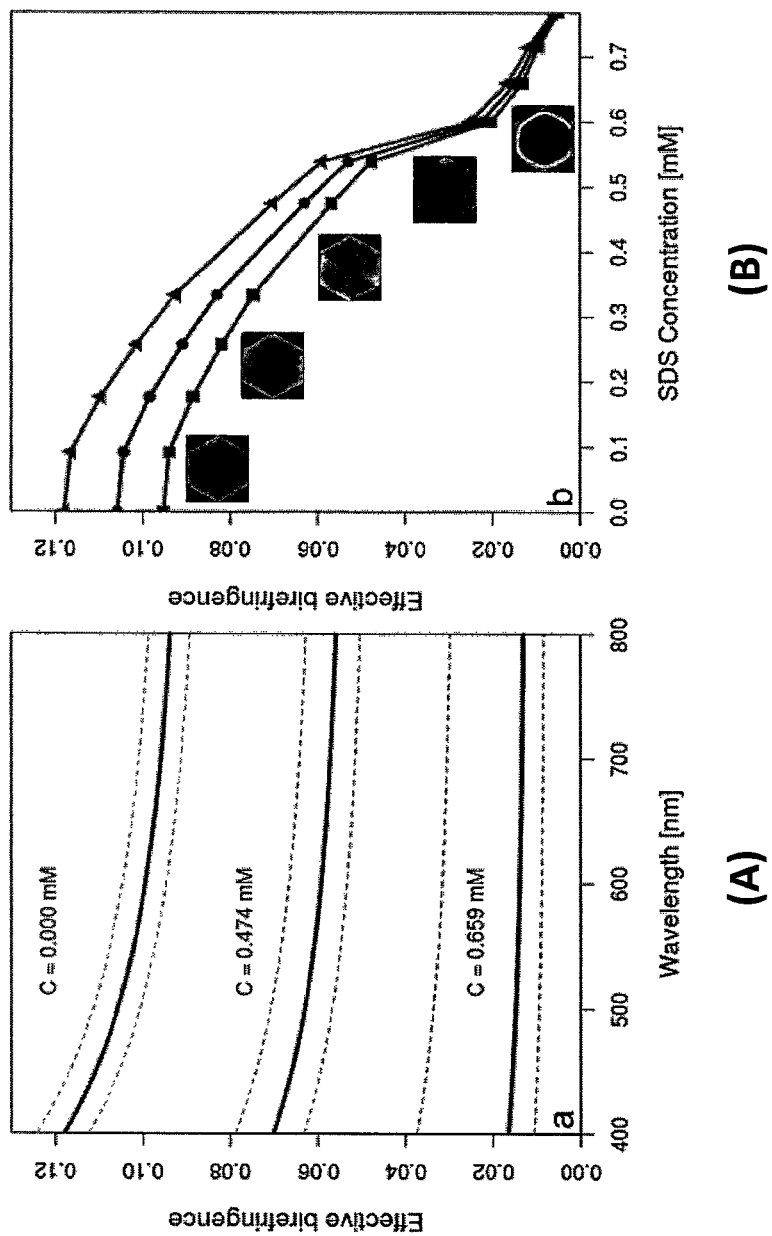
FIG. 12 is (a) a graph of effective birefringence vs. wavelength (nm). The solid curves represent effective birefringence dispersion of 5CB in solution/air at different SDS concentrations. The curves are plotted with dashed uncertainty bands. Also included is (b) a graph of effective birefringence vs. SDS concentration for different wavelength with textures using circular polarizers. The line with squares represents 650 nm, the line with circles represents 510 nm, and the line with triangles represents 400 nm. These measurements are obtained in an experiment using 6 individual LC cells.

Example 4: Effective Birefringence Dispersion of 5CB in Solution/Air at Different SDS Concentrations As illustrated in FIG. 12, quantitative birefringence measurements using circular polarizers are collected in the water-air system with the surfactant SDS added to the water. In FIG. 12(a) the wavelength dependent effective birefringences are plotted with standard deviation bands. Similar to previous observations, dispersion decreases with increasing concentration. The standard deviation increases toward higher concentrations, because the number of peaks decreases and the fit becomes less sensitive. FIG. 12(b) shows the dependence of the SDS concentration on the effective birefringences at three wavelengths. As the concentration increases, the effective birefringence decreases and the dispersion vanishes.

Typical textures seen between circular polarizers are also shown. The results are consistent with the work reported by Iglesias et. al. (W. Iglesias, N. L. Abbott, E. K. Mann, and A. Jákli, ACS Appl. Mater. Interfaces 4, 6884 (2012) in the sense that the SDS concentration needed to switch to homeotropic state is the same, but the birefringence values are slightly higher here. This is partially due to the lower homeotropic anchoring energy at the LC/air interface than at the LC/polymer interface, and partially because the effective birefringence is averaged only over carefully selected cells and not the entire grid.

Example 5: A "Dynamic" Mode of Sensing DLPC Phospholipid

Figure 13:
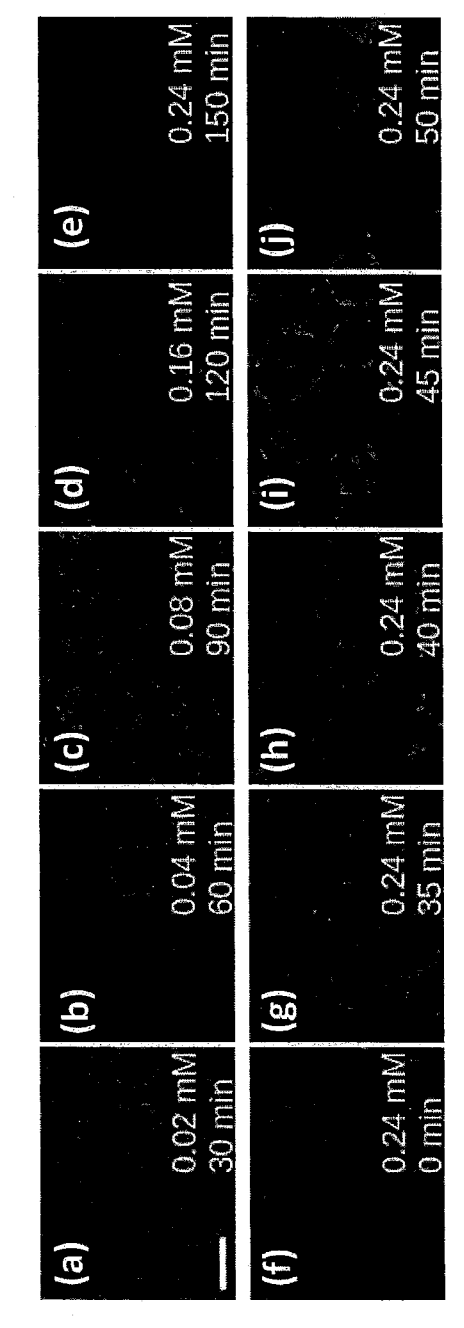

As illustrated in FIG. 13, the dynamics of the sensor, and in particular the time to reach equilibrium of surface-active molecules with the LC/solution interface, depends on the concentration of the surfactant: the lower is the concentration the more time is needed. For this reason, although typically 30 minutes waiting time is sufficient, data points of FIG. 12(b) were obtained after 60 minutes waiting time. With insufficient waiting time the graph in FIG. 12(b) would exhibit a plateau for low surfactant concentration and the biosensor would be regarded as insensitive in that range.

Although the response time of an LC-based biosensor can be shortened either by decreasing the thickness of the LC films, or by increasing the temperature, in some cases it still can be too slow. For example in case of the phospholipid, DLPC (CMC=90 nM) even the lowest 0.02 mM concentration used is about 200 times higher than the critical micelle concentration of the DLPC. The director orientation transitions completely to the homeotropic state given enough time, but this transition takes about one day. For this reason, instead of studying the concentration dependence after very long waiting times, the concentration dependence of the texture (and birefringence) after constant (30 minutes) increments of waiting times was studied.

The qualitative POM results are shown in the top row of FIG. 13. The texture changes by nucleation and growth of domains when lipid concentration is increased slowly, and reaches the dark state only at 0.24 mM concentration. When DLPC is added in 0.24 mM concentration initially, no nucleating domains appear and the texture becomes uniformly darker with time, reaching a nearly homeotropic state in about 50 minutes (see FIG. 12 bottom row). These clear differences between the different concentrations indicate that, depending on the dynamics and concentration range of the surfactant, one may use the LC-based biosensor in a "steady" mode, which was studied by Kinsinger et. al. by depositing the lipid Langmuir monolayers at a fixed density (M. I. Kinsinger, D. M. Lynn, and N. L. Abbott, Soft Matter 6, 4095 (2010), or could switch to a "dynamic" mode, where the sensing range depends on the rate of the concentration change. A fast rate will be able to distinguish between large concentrations, with low concentrations hardly registering, while a slow rate can distinguish between low concentrations, with higher ones saturating the signal. For very small amphiphile concentrations one should change the concentration at a low rate, while for larger concentrations a higher rate could be used. The introduction of this new "dynamic" mode therefore allows setting the range of the sensitivity.

Example 6: Smectic Phase

The concentration range over which a biosensor is sensitive to lipid quantity may be enhanced, towards both higher and lower concentrations, when the liquid crystal is cooled to the Smectic A (SmA) phase.

An example for the increased sensitivity to low quantity ranges was demonstrated for the liquid crystal 4-N-Octyl-4-CyanoBiphenyl (8CB) that has a I 40.5° C. N 32° C. smectic A phase sequence. The formula for 8CB is illustrated below:

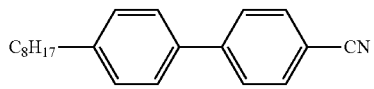

Figure 14:
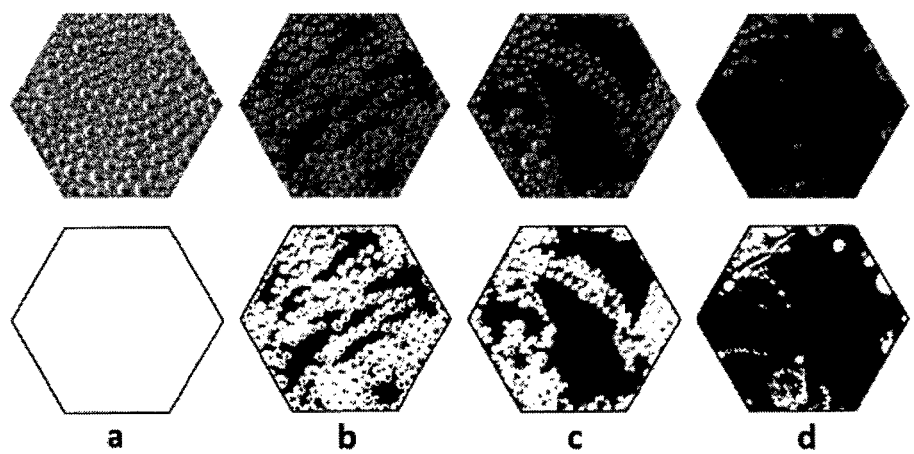
FIG. 14 illustrates example textures in smectic phase as seen under a microscope using polarizers.

When DPLC was added to water at very low concentrations (from about 0.05 µM to about 1 µM), the surfactant could not be detected in the nematic phase. However, when it is cooled to the SmA phase, an inhomogeneous texture including focal conic domains characteristic to SmA between pure water-air interfaces and homeotropic domains characteristic of air-air or air/surfactant substrates appeared. FIG. 14 illustrates these textures. The top row shows example textures in smectic phase as seen under a microscope using circular polarizers. The bottom row includes black and white representations for textures for calculation of the ratio of homeotropic region coverage S[%]. In FIG. 14, (a) is pure water S≈0%; (b) is 0.1 µM of DPLC after 10 minutes—S=31±2%; (c) is 0.1 µM of DPLC after 30 minutes—S=44±2%; and (d) is 0.1 µM of DPLC after 90 minutes—S=58±4%. The TEM grid was in contact with an aqueous solution (dispersion) at the bottom and in contact with air at the top. The cell diameter was about 200 µm.

Using the black and white representations of the bottom row of FIG. 14, the homeotropic (black) coverage area was defined as $$S = \frac{\text{black pixels}}{\text{black pixels} + \text{white pixels}} \times 100\%.$$

Figure 15:
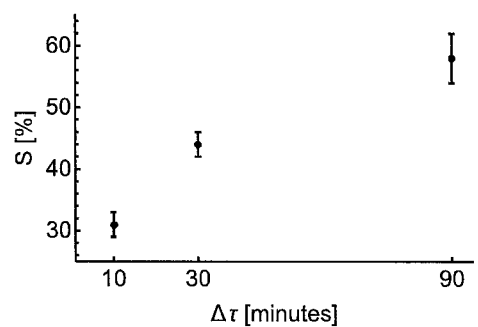
FIG. 15 is a graph showing homeotropic coverage ratio in smectic phase versus time of phospholipid adsorption.

The time dependence of S is plotted in FIG. 15.

FIG. 15 illustrates the homeotropic coverage ratio in smectic phase versus time of phospholipid adsorption to 8CB/water interface. Concentration of DLPC phospholipid was kept at 0.1 µM. The uncertainty bars come from S values of 7 cells that are located at the center of the grid. Experiments were performed 3 times for each point, so that effectively averaging was done over 21 cells for each point.

Figure 16:
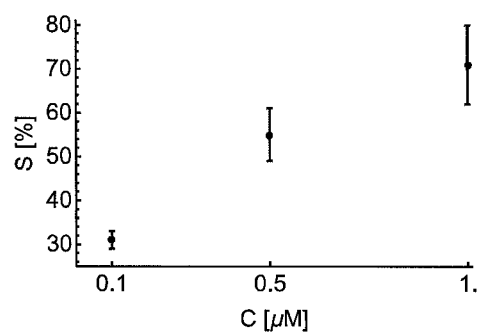
FIG. 16 is a graph showing homeotropic coverage ratio in smectic phase versus concentration of phospholipid in the bulk of water.

Additionally, the concentration dependence of S after a fixed time interval of 10 minutes was evaluated. The results are provided in FIG. 16. FIG. 16 illustrates the homeotropic coverage ratio in smectic phase versus concentration of phospholipid in the bulk of water. Data was collected after 10 minutes of DLPC adsorption to 8CB/interface. The uncertainty bars come from S values of 7 cells that are located at the center of the grid. Experiments were conducted 3 times for each point, so that effectively averaging was done over 21 cells for each point.

Figure 17:
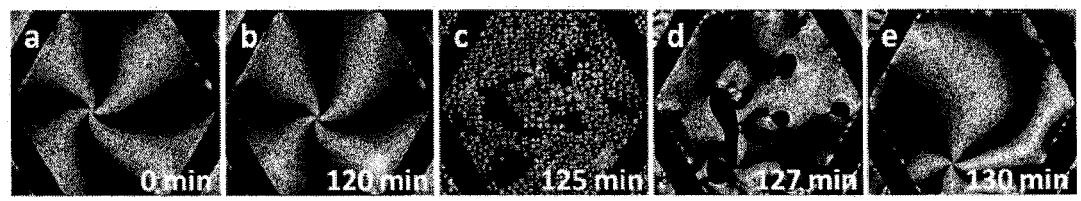
FIG. 17 illustrates the response of 8CB to DLPC solution at 0.05 μM.

After heating the sample back to nematic state, the dark regions disappeared within about 1 minute and the film appeared again as if there was no lipid present. FIG. 17 illustrates the response of 8CB to DLPC solution at 0.05 µM. The cell diameter was about 430 µm. The pictures were taken between linear crossed polarizers.

Upon heating 8CB to the nematic state, the texture showed a response to DLPC at higher concentrations and/or after much longer waiting time than in the SmA phase. For example, at 0.1 µM of DLPC, the nematic 8CB started responding only after about 1.5 hours, or alternatively, after 10 minutes a response could only be observed if the concentration of DLPC was more than 1 µM.

Figure 18:
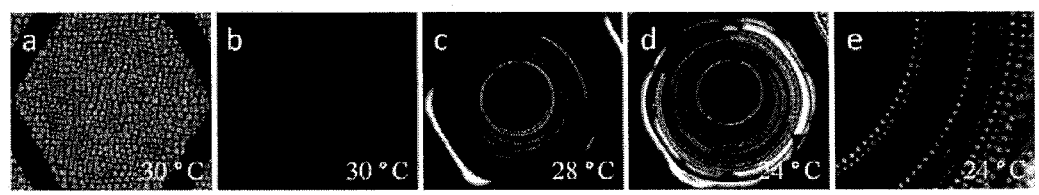
FIG. 18 illustrates the response of 8CB film at different temperatures in the smectic phase.

An example to illustrate the extension of the detection range toward higher concentrations is shown in FIG. 18. The DLPC concentration was so large (50 µM) that the alignment was already completely homeotropic in the namatic phase (the sensor is saturated), and because unsaturated when cooled to the SmA phase, wherein—in addition to the homeotropic state that characterizes the SmA phase in between air-air substrates—a birefringence ring pattern formed. FIG. 18 illustrates the response of 8CB film at different temperatures in the smectic phase. The cell diameter was about 430 µm in pictures (a) and (b). Picture (e) shows a magnified section of about 30×40 µm² area of picture (d) to resolve the structure of the rings.

Example 7: Cholesteric Phase

Biological materials are chiral. Therefore, they can interact sensitively and specifically with chiral liquid crystal films, such as cholesteric liquid crystal films.

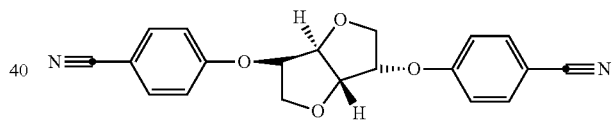

Figure 19:
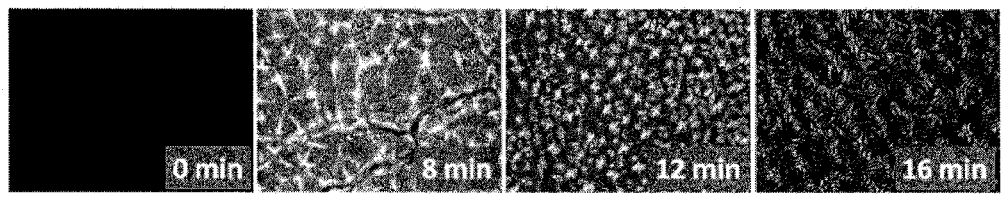
FIG. 19 illustrates the effect of DLPC solution with a concentration of 50 μM at different short-scale times.

5CB was doped with the chiral dopant KDI-6-A at 5 wt % concentration. KDI-6-A is of the formula $C_{20}H_{16}N_2O_4$, has a molecular weight of 348.55, a melting point of 135-137° C., and a helical twisting power (HTP) of about 4 µm⁻¹. The doping resulted in a chiral nematic phase with a helical pitch of about 5 µm. FIG. 19 illustrates the effect of DLPC solution with a concentration of 50 µM at different shortscale times (much less than the time needed to equilibrium texture) after contact with both LC (5CB) surfaces (grid immersed in solution). The cell diameter was about 430 µm. The cholesteric films were viewed with circular right/left polarizers under a magnification of about 400×.

The texture shows concentric interference rings before the lipid diffuses to the LC interface. The texture transforms to a fingerprint texture as the lipid reaches the interface. This is the sign of the realignment of the LC in N* phase from a planar to a tilted orientation. Eventually, after a very long time, the LC alignment becomes homeotropic, which leads to the coexistence of fingerprint/homeotropic textures where the helix is partially or completely unwound by the lipid.

Figure 20:
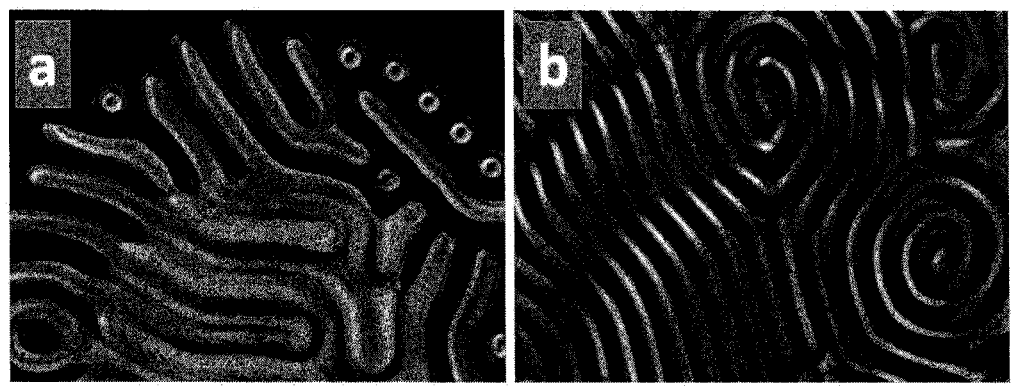
FIG. 20 illustrates some examples of terminal fingerprint LC textures after 12 hours.

FIG. 20 illustrates typical terminal fingerprint LC textures after 12 hours. A DPLC solution at a concentration of 50 µM made in contact with both LC surfaces (grid immersed in solution). The cholesteric films were viewed with circular right/left polarizers at a magnification of about 400× (equilibrium states). The cell diameter was about 430 µm.

While detection of amphiphiles is described, it will be appreciated that aspects of the disclosed approaches are readily applied to detection of other analytes that collect as surfactants on the LC surface and induce changes in birefringence of the bulk LC. In such cases generally, the use of—circular polarizers of opposite handedness, rather than crossed linear polarizers, removes the impact of additional information regarding the director which is difficult to control, so as to provide more accurate quantitative results. As a consequence, it is possible to perform the sensing on a per-cell basis (e.g., per-cell of a TEM grid) rather than requiring averaging over multiple cells to statistically remove the impact of the additional information regarding the director. This in turn allows improved data collection and analysis as further disclosed herein, for example collecting measurements for different interfacial conditions using different cells so that film thickness and the effective birefringence can be determined separately.

In the following, further disclosure is set forth in the form of one-sentence statements having the general form of patent claims ("CLAIMS").

The invention claimed is:

1. A method for detecting amphiphiles at a liquid crystal water interface, comprising:
    shining collimated white light on an LC cell including an LC film;
    polarizing the white light with a circular polarizer;
    adding an amphiphile to a solution in contact with the LC film;
    optically detecting the presence of the amphiphile by measuring a change in birefringence exhibited by the LC film; and
    measuring a dark state signal ($D_\lambda$) wherein the LC cell is in contact with air at a first interface and second interface.

2. The method according to claim 1, wherein the LC film is substantially aligned in a homeotropic configuration.

3. The method according to claim 1, wherein a bright reference state signal ($R_\lambda$) is measured by removing either a linear or the circular polarizer.

4. The method according to claim 3, wherein a percent transmission ($T_\lambda$) of a resulting signal ($S_\lambda$) is calculated based on the dark state signal and the bright reference state signal.

5. The method according to claim 4, wherein the percent transmission ($T_\lambda$) may be used to determine birefringence and its dispersion relation.

6. The method according to claim 5, wherein the transmitted light intensity is measured in the presence of the LC cell in contact with water at a first and second interface.

7. The method according to claim 6, wherein the LC film is substantially aligned in a parallel configuration.

8. The method according to claim 6, further including evaporating the first interface and adding an amphiphile to the water in the second interface.

9. The method according to claim 8, wherein the amphiphile is added to the second interface at a constant rate in order to provide a dynamic mode of detection.

10. The method according to claim 1, wherein the LC film is a smectic phase LC film.

11. The method according to claim 1, wherein the LC film is a cholesteric phase LC film.

* * * * *

UNITED STATES PATENT AND TRADEMARK OFFICE
CERTIFICATE OF CORRECTION

| | |
|---|---|
| PATENT NO. | : 9,689,793 B2 |
| APPLICATION NO. | : 14/621837 |
| DATED | : June 27, 2017 |
| INVENTOR(S) | : Antal Jakli, Elizabeth Mann and Piotr Popov |

It is certified that error appears in the above-identified patent and that said Letters Patent is hereby corrected as shown below:

In the Specification

Insert at Column 1, Line 12, the following paragraph heading and paragraph:
--STATEMENT REGARDING FEDERALLY SPONSORED RESEARCH
The invention was made with government support under Grant No. DMR-0907055 awarded by the National Science Foundation. The government has certain rights in this invention.--

Signed and Sealed this
Fifteenth Day of October, 2024

Katherine Kelly Vidal
*Director of the United States Patent and Trademark Office*